United States Patent [19]
Kaplan

[11] Patent Number: 6,033,568
[45] Date of Patent: Mar. 7, 2000

[54] BIOREACTOR AND METHOD OF MEASURING CONTAMINANTS IN AN AQUEOUS ENVIRONMENT

[75] Inventor: Louis A. Kaplan, West Grove, Pa.

[73] Assignee: Stroud Water Research Center, Inc., Avondale, Pa.

[21] Appl. No.: 09/175,512

[22] Filed: Oct. 20, 1998

Related U.S. Application Data

[62] Division of application No. 08/733,253, Oct. 18, 1996, Pat. No. 5,873,997.

[51] Int. Cl.[7] ....................................................... C02F 3/32
[52] U.S. Cl. .......................... 210/602; 210/615; 210/908; 210/921; 436/146
[58] Field of Search ..................................... 210/602, 615, 210/908, 921; 436/146

[56] References Cited

U.S. PATENT DOCUMENTS

| | | |
|---|---|---|
| 3,232,434 | 2/1966 | Albersmeyer . |
| 3,751,167 | 8/1973 | Claus ......................................... 356/51 |
| 4,009,105 | 2/1977 | Jeris ........................................ 210/107 |
| 4,211,647 | 7/1980 | Friedman et al. . |
| 4,292,171 | 9/1981 | Smith et al. . |
| 4,690,755 | 9/1987 | Friedman et al. . |
| 4,775,634 | 10/1988 | Sienkiewicz ............................. 436/146 |
| 5,064,534 | 11/1991 | Busch et al. . |
| 5,441,642 | 8/1995 | Wickens . |
| 5,482,630 | 1/1996 | Lee et al. . |
| 5,496,460 | 3/1996 | Jorgenson et al. . |
| 5,525,228 | 6/1996 | Dague et al. . |

OTHER PUBLICATIONS

Kaplan LA, Ribas F, Joret JC, Volk C, Frias J, and Lucena F. Measurement of Biodegradable Organic Matter with Biofilm Reactors. AWWA Research Foundation; Apr. 1996.

Kaplan LA and Newbold JD. Measurement of Streamwater Biogradable Dissolved Organic Carbon with a Plug–Flow Bioreactor. Oct. 19, 1995.

Ribas F, Frias J and Lucena F. A New Dynamic Method for the Rapid Determination of the Biogradable Dissolved Organic Carbon in Drinking Water. 1991.

Lucena F, Frias J and Ribas F. A New Dynamic Approach to the Determination of Biodegradable Dissolved Organic Carbon in Water. 1990.

Literature page from CHROMAFLEX Columns Catalog.

*Primary Examiner*—David A. Simmons
*Assistant Examiner*—Betsey J. Morrison
*Attorney, Agent, or Firm*—Paul & Paul

[57] ABSTRACT

A method and apparatus are provided for measuring the concentration of contaminants in an aqueous water system, wherein the contaminants are measured with the bioreactor containing a biofilm or microbial community which acts on the water to be analyzed to provide a measure of the amount of the dissolved organic carbon which is biodegradable. A bed for facilitating regulation of water flow through the bioreactor is provided, and an autosampling mechanism enables the measurement of total organic carbon, inorganic carbon and oxygen, between sample inflow and sample outflow at specified time intervals.

9 Claims, 4 Drawing Sheets

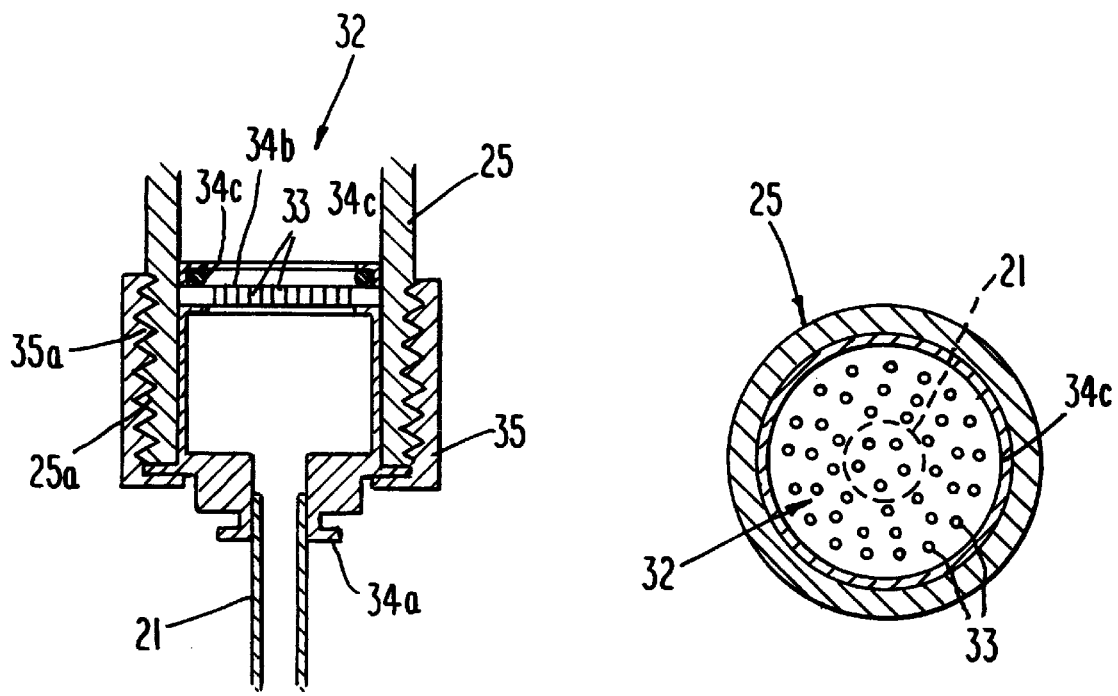
*Fig. 3*  *Fig. 3a*
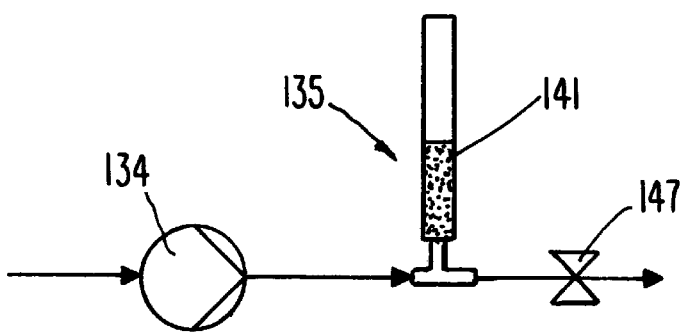
*Fig. 4*

BIOREACTOR AND METHOD OF MEASURING CONTAMINANTS IN AN AQUEOUS ENVIRONMENT

CROSS REFERENCE TO RELATED APPLICATIONS

This application is a divisional continuation of U.S. application Ser. No. 08/733,253, filed on Oct. 18, 1996 now U.S. Pat. No. 5,873,497 issued Feb. 23, 1999.

BACKGROUND OF INVENTION

1. Field of Invention

The present invention relates to the field of water contaminant and treatment measurements.

2. Brief Description of the Prior Art

Analyzing contaminants in a water supply can often take significant time to complete, and furthermore is often difficult to carry out. Present techniques and apparatus generally require much time to obtain measurements or readings of water supply contaminants. Water utilities are confronted with the task of maintaining contaminants at reduced levels, while, at the same time, controlling the levels of treatment compounds to maintain a safe concentration for consumption by users or ultimate discharge of the water into the ecosystem. Often strict government regulations must be met so as to have a minimum acceptable level of contaminants and maximum acceptable levels of treatment chemicals. Coliform bacteria and other contaminants must be carefully monitored and treated. In addition to the treatment compounds themselves added to water, byproducts are often formed from the reaction of these compounds with the contaminants. Therefore, it is not possible to simply add a given amount of treatment chemical to a water supply, rather, the water must be monitored before, as well as after, and even during the treatment process.

Thus the need for accurate, timely analysis of contaminants, treatment chemicals and byproducts in a water system remains important to the ability to provide adequate treatment and management of a water supply.

Dissolved organic matter is an important component in a water system that must be carefully monitored and controlled due to its relationship with the contaminants. The greater the presence of dissolved organic matter in a water system the greater the potential for water contaminants, such as, for example, bacteria and other organisms to proliferate and further contribute to the degree of contamination of a water supply. The effect is more pronounced over time if bacteria and other organisms are allowed to build up. Therefore, measurement of biodegradable organic matter in a water system provides information which can be used to determine the extent and success of disinfectant or treatment to be administered to a water supply.

Biodegradable organic carbon has been measured by a number of different assays as a way of determining the concentrations of biodegradable dissolved organic matter present in the aqueous system. The assays, however, are known to take substantial time. Reliability and rapidness of measurement are desired when monitoring the concentrations of biodegradable organic contaminants at a water utility during the purification or disinfecting treatment process.

SUMMARY OF THE INVENTION

The present invention provides a method and apparatus for measuring concentrations of contaminants in aquatic systems, such as, for example, those present in water utility systems. Biodegradable dissolved organic matter is determined by the present invention. A method and apparatus are provided for measuring levels of organic carbon and inorganic carbon in a water system and utilizing a differential analysis to determine the level of biodegradable organic carbon contained in a water system. The apparatus of the invention provides a bioreactor which is inoculated with microbes to form a biofilm which acts upon the biodegradable organic carbon present in the water to be analyzed. The microbes generally comprise the natural flora and organisms indigenous to the water supply or system to be analyzed. The apparatus includes at least one chromatography column which is packed with a material on which microbes can proliferate. Water flow is directed through the column with a pump. The apparatus and method also facilitate control and regulation of the water passage through the column length. A bed is provided through which the water to be analyzed passes as it enters the column. A microbial inoculum is introduced to the bioreactor and resides on the packing material within the column. The bed provides an even flow of water to the microbes within the column and facilitates uniform water residence time as the water flows through the column.

The microbial community establishes itself within the column, and thereafter can be utilized to measure biological activity with respect to water samples which flow through the bioreactor. A sample of the inflow water is taken and a sample of water is taken at the outflow. The biodegradable dissolved organic carbon (BDOC) present in the water sample is acted upon by the microbes wherein the biodegradable dissolved organic carbon concentration is ascertained by the difference between the readings of DOC concentrations between the inflow and the outflow. The present invention provides a novel sampling apparatus and method wherein continuous and automated readings of DOC concentrations at the inflow and outflow points of the bioreactor are obtained. The apparatus and method also provide means for determining inorganic carbon and organic carbon concentrations, and the concentration of dissolved oxygen in a water sample.

It is an object of the present invention to provide a method and apparatus for determining the concentration of biodegradable organic matter in a water system as a way to measure biodegradable dissolved organic matter in the water system.

It is another object of the present invention to accomplish the above object with a bioreactor.

It is an object of the present invention to provide a novel bioreactor apparatus which can measure concentrations of material affected by the microbial community or biofilm present in the bioreactor.

It is another object of the present invention to provide a bioreactor which can be used to provide accurate readings of biodegradable dissolved organic carbon in an aquatic environment, such as, for example, a drinking water utility processing plant.

It is another object of the present invention to provide a novel method and apparatus for measuring contaminants in an aquatic environment, wherein the measurement can be determined within minutes of taking a sample.

It is another object of the present invention to accomplish the above objects by providing water flow regulating means for regulating the passage of water as it enters and/or exits the bioreactor columns.

It is another object of the present invention to improve the reliability and accuracy of measuring contaminants in an aqueous environment with a bioreactor by maintaining a uniform flow of water to be analyzed as the water sample travels through the column of the reactor.

Another object of the present invention is to decrease the measurement time of ascertaining the concentration of contaminants in an aqueous environment, namely where the contaminants comprise biodegradable dissolved organic matter.

BRIEF DESCRIPTION OF THE DRAWING FIGURES

FIG. 3 is an enlarged sectional view of the column bed of the apparatus of FIG. 1 represented by the box 3 of FIG. 1.

FIG. 3a is a top cross-sectional view of the column of FIG. 3 taken along the line 3a—3a of FIG. 3.

FIG. 4 is a right side schematic view of the damper of the embodiment shown in FIG. 2.

DETAILED DESCRIPTION OF THE PREFERRED EMBODIMENTS

Figure 1:
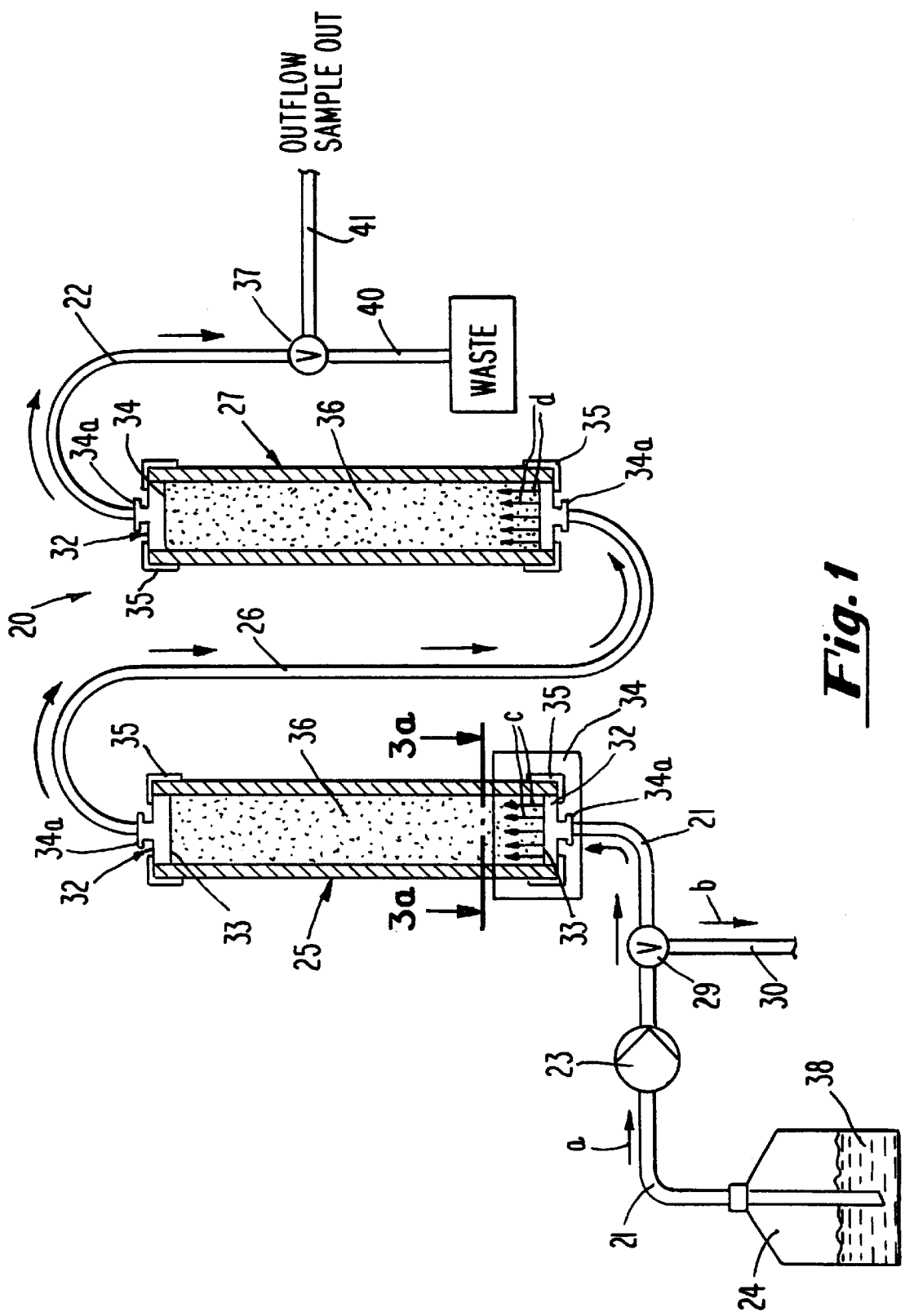
FIG. 1 is a schematic view of a bioreactor according to the present invention, with the bioreactor columns shown in sectional view.

Referring to FIG. 1, a bioreactor 20 according to the present invention is shown comprising a water input line 21, a water output line 22, means for moving the water through the reactor, which is shown comprising an inflow pump 23, which preferably may comprise a peristaltic pump, and first and second columns 25 and 27, respectively. A sample source reservoir 24 is provided in which the water input line 21 extends so that the inflow pump 23 can draw a flow of water from the sample source 24 and move the water along the input flow line 21 for delivery to the first column 25. The sample source, while shown represented as a reservoir 24, is preferably provided as a direct line (not shown) from the water source to be analyzed, such as, for example, any drinking water sources, including, without limitation, reservoirs, streams, wells or springs. The direct line may include one or more filtration steps, as necessary, to remove debris, and/or other components from the water source. Preferably filters used, while not shown, are comprised of materials which do not interfere with organic molecules and microbes, and which permit microbes to pass through into the filtrate. Generally, large particles which might otherwise interfere with the columns or water flow through the bioreactor 20 are desired to be removed.

The inflow pump 23 directs the water through the first column 25, out of the first column 25 through a transition line 26 and into a second column 27. The water inflow represented by arrow "a" may be diverted by an inflow valve 29 shown disposed in line and downstream from the pump 23. The inflow valve 29 is located before the first column 25 and can divert sample flow to the sampling tube 30 in the direction of arrow "b". The sampling tube 30 may be used for collecting spot samples or can be connected in-line for direct delivery of inflow sample to an analyzer, such as that shown in FIG. 2.

The first and second columns 25, 27 are provided with means for regulating and controlling the flow of water through a column. Preferably, as shown in FIG. 1, and in the enlarged view of FIGS. 3 and 3a, is a bed 32 comprising a plurality of apertures 33 through which the water entering the first column 25, for example, is forced. The bed 32 is generally comprised of an end fitting 34a, a bed support 34b, and an o-ring or gasket member 34c. The bed support 34b is placed on the end of the end fitting 34a and is secured with the gasket 34c. The end fitting 34a is then placed onto the end of the column 25. An end cap 35 is placed over the end fitting 34a to secure the bed 32 in place on the end of the column 25. Suitable attachment means is provided for attachment of the bed 32 to the end of the column 25. As shown, the attachment means may, for example, comprise first threads 25a on the outer circumference of the column and matingly associated second threads 35a on the rim of the end cap 35. Preferably, the bed 32 comprises materials which do not interfere with the organic molecules and microorganisms and which do not leach molecules into the system. PTFE is an example of a compound that can be used to comprise the components of the bed 32, as can any other suitable inert material, which will not react, by adsorption, absorption, or otherwise, with the sample water, the microbes or the contaminants in the sample water, and which also will not leach material therefrom. The bed 32 facilitates even dispersion of the sample water through the column 25 represented by the arrows "c", so that water residence time and flow is generally equalized between various vertical zones of travel through the column 25. Since the beds 32 can be the same for each column inflow and outflow, they are generally designated by the numeral 32. Similarly, water flow through second column 27 is shown passing through the bed 32 in the direction of arrows "d". Optionally, while not shown, a water jacketed column can also be used as a way to maintain the temperature of the column.

The first and second columns 25,27 are filled with a packing material, generally 36, which preferably comprises a suitable base on which the microbes (not shown) can proliferate to establish a biofilm or community. The packing material 36 preferably comprises a material which will not react with the water stream, the microbes, or any of the byproducts or contaminants being analyzed. For example, the packing material 36 may comprise a borosilicate glass. Preferably, an open-pored sintered glass material is used, and particularly preferably, open-pored sintered glass having a sphere diameter of about 1 to 2 mm, and a pore diameter of from about 60 to 300 $\mu$m, such as that commercially available in the industry.

The bioreactor 20 is prepared by assembling the components shown in FIG. 1, and then packing the first and second columns 25,27 with the packing material 36. The first column 25 is filled about half-way with the source water, and the packing material 36 is added to fill a couple of centimeters of vertical height of the first column 25, and tapped to settle the packing material 36 within the column. This step is repeated until the first column 25 is fully packed. The bed 32 is placed onto the top of the column 25 as described above (FIGS. 3 and 3a).

Source water is then pumped through the first column 25, through the connecting tube 26 and then through the second column 27, until the second column 27 is about half full. The second column 27 is packed in the same manner as described above in relation to the first column 25, and is then closed with a bed 32.

An output flow valve 37 is provided on the output flow line 22 for diverting output flow from the second column 27 to a waste flow line 40 or to a sample output flow line 41. The sample output flow line 41 may in turn be connected to a sample analyzer for monitoring of the water outflow, such as that shown in FIG. 2.

Preferably, the first and second columns 25,27 are comprised of a non reactive material, such as, for example, borosilicate glass. The flexible tubing utilized to comprise the flow lines can comprise any suitable non-reactive composition, and preferably a polytetrafluoroethylene material is used.

The bioreactor 20 must be inoculated with microbes in order to commence operation. The microbes utilized are those indigenous to the water source to be measured, such as for example a stream (not shown). The inflow of source water 38 into the reactor columns 25,27 introduces the microbes to the bioreactor 20 where they reside on the surfaces of the packing material 36. Generally, the source water 38 is permitted to continuously flow through the bioreactor 20, at a predetermined rate, so that the microbial community or biofilm can be sustained within the bioreactor 20. The bioreactor 20 must undergo a period of up to about four to six months, or sometimes greater, for the microbial community to become established on the packing material 36 surfaces.

Establishment of the microbial community in the bioreactor 20 can be ascertained by repeating a measurement of a water sample containing a known concentration of contaminants until consistent results are obtained. Generally, the biodegradable dissolved organic carbon expressed as a percent of dissolved organic carbon (DOC) which is removed from the water inflow by the action of the microbes in the bioreactor 20 steadily increases from the initial inoculation of the bioreactor 20 with the water containing the microbes until the biofilm has been established, at which time the rate of DOC removal levels off. The biofilm establishment time depends on the type of contaminants and organisms present, as well as other factors which might have an effect on the microbial metabolism rate, such as, for example, temperature and season of year.

Measurement of the DOC concentration can be performed by taking a reading of the inflow and the outflow and determining the difference in the concentration of DOC. The microbes in the bioreactor 20 will consume DOC. Therefore, if the total concentration of organic carbon of the inflow is known, the difference in the organic carbon reading from the outflow provides a measure of the concentration of biodegradable dissolved organic carbon (BDOC). The measurement obtained is a net measurement because the microbes, while consuming organic molecules, excrete some organic molecules, as well, such as for example, waste products. Therefore, the measurement of BDOC which appears to be consumed actually represents some organic matter which is consumed by the microbes and some organic matter which the microbes have produced as byproducts of metabolism.

Once established, the bioreactor 20 can be utilized to ascertain the concentration of biodegradable organic matter present in the water system. The water sample 38, or stream, to be analyzed is pumped through the columns 25,27 and samples taken at the inflow and at the outflow to measure the concentrations of contaminants present in the form of organic carbon molecules. Inorganic carbon (IC) can also be determined as a check on the microbe activity. The net change in organic carbon between the concentration of the inflow versus the concentration of the outflow is representative of biodegradable dissolved organic matter, which has been metabolized (although a minor amount of the organic carbon may actually have been a byproduct of microbial metabolism the reading obtained is generally accepted as an underestimate of BDOC contaminant).

Figure 2:
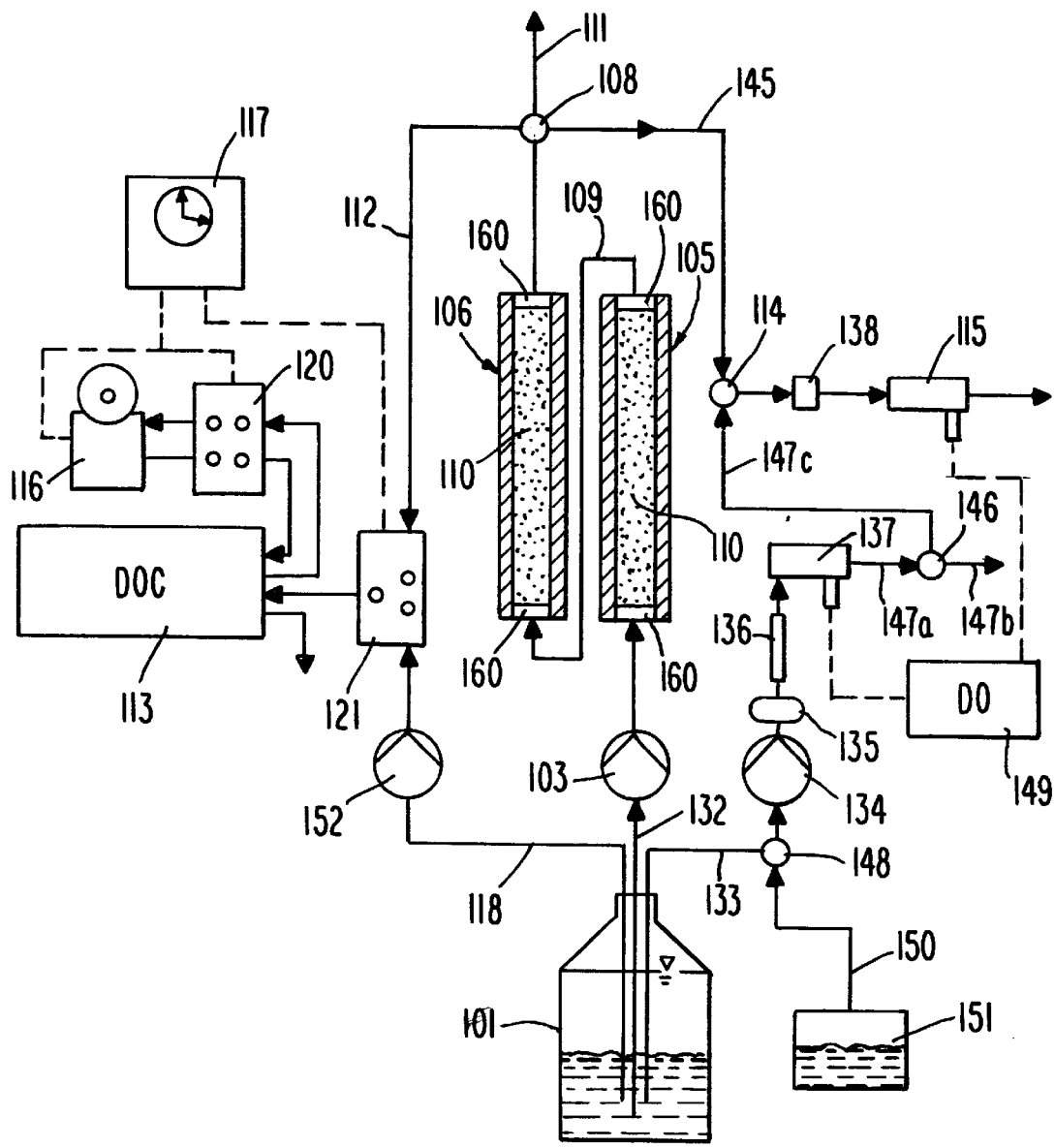
FIG. 2 is an alternate embodiment of a bioreactor according to the present invention with an autosampling mechanism.

A preferred sampling and measuring apparatus is shown in FIG. 2. A bioreactor 100 with auto sampling capabilities is shown in partial schematic view. The water supply source for sampling is generally represented by the reservoir 101, but can comprise a direct line from a stream well or other water supply to be analyzed. An inflow line 102 extends from the sample reservoir 101 or stream to a sample inflow pump 103 which operates to draw water from the sample source 101 and moves the water through the reactor first and second columns 105,106. The first and second columns 105,106 are preferably provided with the flow regulation means described above in relation to FIGS. 3 and 3a, and shown comprising the bed 32. The flow regulation means facilitates an even flow of sample water through the first and second columns 105,106 to provide uniform residence time for sample contact with the biofilm established within the first and second columns 105,106. The bed 160 can be provided to be of the same construction as the bed 32 described above and shown in FIGS. 3 and 3a.

Sample water flows into the first column 105, and then through a transition tube 109 connecting the columns 105, 106 and through the second column outflow tube 107. The transition tube 109 makes it possible for there to be an additional sampling point between the columns 105,106. The second column outflow line 107 flows into an output flow diverter valve 108 which can be operated to divert the flow exiting the second column 106. As shown in FIG. 2, three paths of travel are possible from the diverter valve 108. The output flow diverter valve 108 may be manually operated or can be automatically operated in conjunction with a timer or other mechanical or electronic means. A waste line 111 is connected to the output flow diverter valve 108 to provide a further path of travel. A flow line 112 is also provided as a further path of travel for the sample flow coming out of the second column 106, which flow line 112 leads to a TOC analyzer 113. The third path of travel shown from the diverter valve 108 connects to an oxygen flow cell valve 114 which regulates passage through an oxygen flow cell 115.

The dissolved organic carbon (DOC) concentration of the water samples to be analyzed with the bioreactor 100, is ascertained with the use of a DOC analyzer 113. The analyzer 113 receives sample and through the use of UV radiation and a chemical oxidizing reagent, such as, for example, ammonium persulfate, measures the amount of formed carbon dioxide resulting from the oxidation of the carbon containing compounds present in the sample. Such analyzers are commercially available, such as, for example, a Sievers model 800 TOC analyzer. The concentration of the organic compounds present in the water sample is measured by the TOC analyzer 113.

Since the calculation is determined by taking the difference between the total carbon and the inorganic carbon to ascertain the total organic carbon, if high levels of inorganic carbon are present in the water samples, then the total organic carbon measurement is overestimated. An inorganic carbon (IC) removal module 116 is provided to remove the inorganic carbon from the sample. The removal module 116 may comprise a vacuum degassing module which has the capability of removing approximately 99% of the inorganic carbon in the sample. Unamended sample flows into the IC removal module 116 and is degassed and the sample is then sent to the TOC analyzer 113 where it is acidified and analyzed for dissolved organic carbon. The IC removal module 116 can be commercially purchased as a Sievers ICR Module 800 (Inorganic Carbon Removal Module).

Readings are taken of total organic carbon (TOC) and inorganic carbon (IC) for each sample. A timer 117 is provided to control the flow path of the water sample to be analyzed by selecting between two flow paths. The timer 117 preferably comprises a digital two channel timer which can be set to regulate the flow of the sample to pass through the IC removal module 116 for a reading of TOC or to bypass the removal module 116 for reading of IC. The first channel of the timer 117 changes between selection of flow from the inflow line 118 and flow through the outflow line 112 of the bioreactor 100. The second channel selects whether the TOC is measured with IC present or after IC removal has taken place. This permits selection between measurements of TOC and IC, as well. The selection of channels is time-based and can be preset. A selection valve 120, which preferably comprises an electrically controlled two-way position valve switcher, connects the TOC analyzer 113 with the IC removal module 116. The selection valve 120 is switched to permit the flow of sample through the IC removal module 116 for the TOC measurement. For the IC measurement, the removal module 116 is bypassed and the module 116 is switched off. The preferred time of operation for TOC and IC measurement is one hour. The timer 117 can therefore be set to alternate between uninterrupted flow to the analyzer 113 and flow through the IC removal module 116, prior to the flow to the analyzer 113.

The second channel regulates timed selection between sample inflow and sample outflow through an inflow/outflow valve 121. For example, the second channel of the timer 117 can be set to change between inflow and outflow every two hours, so that for two hours the inflow is sampled and for the next two hours the outflow is sampled. Other times can be used depending on the TOC concentration, column size and the residence time required for the microbes in the bioreactor 100 to act on the biodegradable dissolved organic carbon.

In addition, while the IC reading operates as a check on biofilm activity, the IC readings can be done less frequently than the TOC readings, with the timer 17 adjusted accordingly.

As shown in FIG. 2, an oxygen monitoring system, generally 130, is provided. The oxygen monitoring system 130 can be provided in line with the bioreactor flow paths to receive sample inflow and sample outflow for analysis of oxygen content. The sample may flow through the analyzer inflow line 118 wherein inflow sample is drawn through the inflow/outflow valve 121 for measurement with the TOC analyzer 113, as discussed above. Sample may also be moved through the column inflow line 132 with the inflow pump 103. Sample can be drawn through the column inflow line 132 with the inflow pump 103 and then moved through the first column 105, through the connecting tube 109 and through the second column 106. The inflow pump 103 can be preset to a desired flow rate to provide adequate residence time of the sample water in the columns 105,106 so that the microbes can act on the molecules in the sample. In addition, while not shown, an inflow selection valve may be provided to permit one or more of the analyzer inflow line 118 and/or the oxygen analyzer flow line 133 to receive a flow at the same time, in addition to the flow to the column 105 through the column inflow line 132, which must be continuously maintained. An oxygen analyzer flow line 133 is connected to a oxygen monitoring system inflow pump 134 which sends an inflow sample through the oxygen monitoring system 130.

A pulse damper 135 is provided to receive the flow from the oxygen monitoring system inflow pump 134, whereupon the flow is directed next through a temperature control means, shown in FIG. 2 comprising an inflow water jacket 136 and an outflow water jacket 138. The oxygen monitoring system includes an inflow cell 137 and an outflow cell 115. Water inflow sample enters the inflow cell 137 after passing through the water jacket 136 as shown in FIG. 2. An outflow cell 115 receives sample outflow from the second column 106 through the oxygen flow cell valve 114. The oxygen monitoring system inflow pump 134 supplies an oxygen inflow cell 137 with sample water. The inflow cell 137 and the outflow cell 115 each contain an electrode which is used to give rise to an electrical potential which is in turn is detected by an amplifier 149. The amplifier 149 can be any of those commercially available for reading the potential from the flow cell electrodes, such as for example the Instech Dual Oxygen Electrode Amplifier Model 203. A pulse damper 135 is provided in the flow path before the inflow cell 137. The damper 135 facilitates an even response by minimizing strong flow variations and variations in the measurement response.

FIG. 4 shows the damper unit 135 in an enlarged view comprising compensation tubing 141 and a resistance unit 142 shown after the pump 134. The resistance unit preferably comprises an adjustable clamp or other suitable narrowing element which constricts the flow through the line 143. The material comprising the damper components generally must not react with the molecules to be measured or affect the biofilm or leach any material into the system.

The second electrode 115 is connected alternatively with the outflow through the outflow oxygen monitoring line 145 or directly with the first electrode 137 of the inflow. This arrangement provides for the calibration of both electrodes 137,115 at the same time. The first electrode of the inflow cell 137 has an outlet line 147a through which the sample passes, which in turn is connected to an interrupt valve 146 which can be set in one of two positions as shown, to dispense the sample to a waste line 147b or to permit sample flow to the second electrode 115 through the transition line 147c. The oxygen flow cell valve 114 located before the second electrode of the outflow cell 115 can be operated to permit the sample flow from the inflow cell 137 to enter the outflow cell 115.

The amplifier 149 measures the response from the first and second electrodes, 137 and 115, respectively. The electrodes 137, 115 are in line oxygen electrodes and are provided to measure in real time with the system flow. The response or signal detected by the amplifier 149 can be further integrated by a recording device (not shown) to calculate a reading corresponding to the oxygen content of the sample.

It is often necessary to calibrate the first and second electrodes 137, 115, which is done by bypassing the bioreactor columns 105,106 with the oxygen monitoring system calibration valve 148 set to close the inflow line 133 and draw calibration standard 151 from the calibration flow line 150. Also, the oxygen flow cell valve 114 is closed to prevent outflow from entering the oxygen monitoring system 130. Preferably, the calibration standard 151 comprises oxygen saturated water.

The measurement of TOC was obtained by taking the data stored on the TOC analyzer 113 and processing it to obtain concentration values over time for the sample. The activity and metabolism of the bacteria is observed over time, and the concentration of BDOC can be ascertained to evaluate the contaminant level present in the water supply being analyzed.

The bioreactor 100 is prepared for operation by first introducing a flow of water from the source, such as for example, a stream, which is to be analyzed. Conditions for preparation and operation of the bioreactor 100 require darkness, so as to prevent light from activating any algae which might be present in the water source or in the column. Also, any water to enter the bioreactor which contains disinfectant, such as chlorine or the like, must first be neutralized to prevent destruction of the biofilm. The water from the source is then pumped through the reactor columns. Preferably, this is done at a flow rate of about 2 to 4 ml/min. This can be done by attaching a direct supply line from the stream to the pump 103 or can be achieved by providing a line from a sample reservoir 101 containing the source water. The water must be maintained at a continuous rate of flow through the reactor in order to allow the bacteria and other organisms in the water to inhabit the packing material 110 of the columns 105,106. This generally takes approximately four to six months, after which time, the bioreactor 100 is ready for use. The flow of source water must also be continuously maintained through the bioreactor 100 even when no measurements are to be taken, in order to enable the biofilm to maintain a state of equilibrium.

The measurement of contaminants in a water supply is an ongoing task. The inoculated bioreactor 100 is provided with a flow of sample from the reservoir 101 or water source which was used to provide the inoculum for the bioreactor 100. For example, in instances where treatment chemical disinfectant has been added to the water supply, the bioreactor 100 can be used to determine the BDOC level. The water from the reservoir 101 is made to flow through the bioreactor 100 by the use of the pump 103. Preferred flow rates of from about 2 to 4 ml/min. are generally used for a bioreactor in which the columns 105,106 are about 2 to 3 cm in diameter and 40 to 70 cm in height. Columns with different size dimensions can also be employed, and other flow rates, both greater and slower can be used. For example, a single column can also be used. The flow rate can be determined by the volume of the column and can be regulated with the pump to achieve uniform flow rates if different column sizes and numbers are used.

Water to be measured is permitted to flow through the bioreactor columns 105,106. The diverter valve 108 is operated to permit sample outflow from the second column 106 to enter the inflow/outflow control valve 121. The control valve 121 accepts the outflow sample and permits the sample to further pass to the DOC analyzer 113, whereupon the sample is run through a subchannel flow path which leads to the IC/DOC valve 120. The IC/DOC valve 120 is operated with the timer 117 to control the flow to one of two possible paths, one which IC removal takes place and another which IC is not removed. As noted above the timer 117 has two channels and generally the second channel regulates the flow through the IC removal module 116 to either send the sample to the IC removal module 116 for removal of IC or to bypass IC removal and permit the sample to flow directly to the analyzer 113. If the sample is directed through the IC removal path, the sample is then analyzed after the IC removal. Generally, the timer channel regulating the IC module flow is switched on an hourly basis to provide an hour of IC removed sample analysis and an hour of IC present sample analysis.

The above described sampling procedure with respect to the IC removal described in connection with sample outflow is also done with respect to the inflow sample. In that case inflow sample from the DOC inflow line 18 is moved to the inflow/outflow valve 121 with the use of the pump 152. The inflow undergoes the same sampling procedures as described above in relation to the outflow sampling analysis and the IC removal module. 116. The inflow sample is measured by the DOC analyzer 113 to provide readings of carbon concentration for sample inflow with and without removal of inorganic carbon.

EXAMPLE 1

Figure 5:
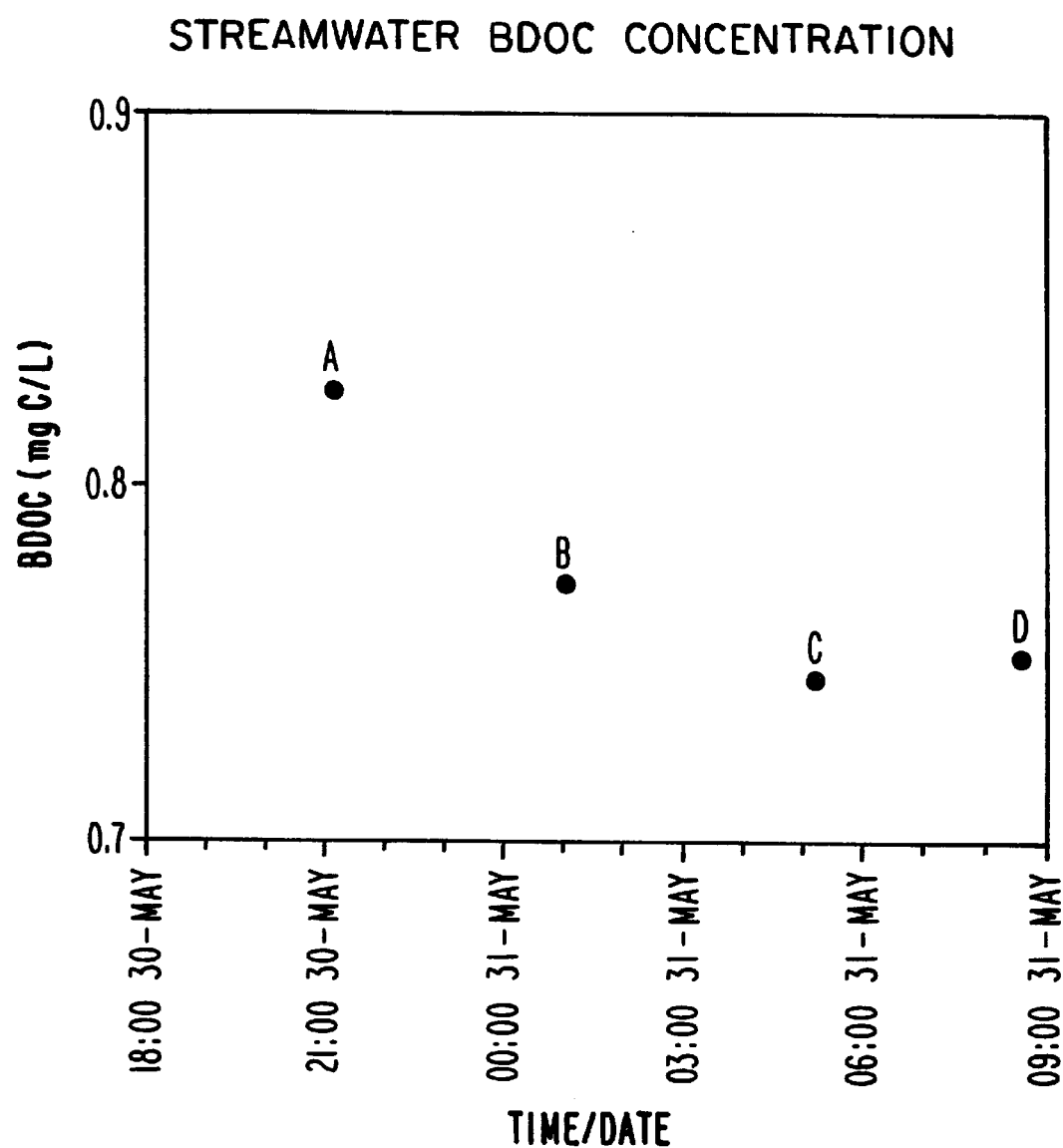
FIG. 5 is a graph of stream water BDOC concentration expressed as a function of time for the results of Table 1.

The following data was generated with water from White Clay Creek, located in southeastern Pennsylvania. The flow rate was maintained at 4 ml/min. The columns used were two borosilicate glass tubes each having an internal diameter of 2.5 cm and a length of 60 cm, sold under the name Chromaflex® by Kontes. The packing material comprised open pored sintered glass of 1–2 mm sphere diameter, 60–300 $\mu$m pore diameter, unmodified, which is sold under the name Siran™ by Schott. PTFE tubing used to connect the pumps, valves and columns in the arrangement described above and shown in FIG. 2. The bioreactor was inoculated by pumping water from the White Clay Creek through a filter system including a first 25 $\mu$m filter in line with a second 0.3 $\mu$m filter, and then through the columns. This was done in the absence of light and for a period of four months after which time the bioreactor was colonized. When the reactor was inoculated and the biofilm formed, a sample of the White Clay Creek water was drawn into the bioreactor with the inflow pump and pumped through the columns at a rate of 4 ml/min. The readings were taken and recorded in Table 1 below, and the total organic carbon (TOC) in mgC/l, ascertained by taking the difference between (i) the average of the first six values of TOCin and (ii) the average of the next six TOCout values to obtain the first point "A" on Graph 1 (FIG. 5). Subsequent readings in the same manner, listed in Table 1, produced points "B", "C", and "D". The readings represent sample from which the IC was removed by the IC removal module.

TABLE 1

Data Used to Calculate Stream water BDOC Concentration

| | | TOC (mgC/L) | |
|---|---|---|---|
| Date | Time | In | Out |
| 5/30/96 | 18:35 | 2.725 | |
| | 18:41 | 2.706 | |
| | 18:47 | 2.665 | |
| | 18:53 | 2.673 | |
| | 18:59 | 2.671 | |
| | 19:05 | 2.679 | |
| | 20:29 | | 1.869 |
| | 20:35 | | 1.858 |
| | 20:41 | | 1.859 |
| | 20:47 | | 1.864 |
| | 20:53 | | 1.865 |
| | 20:59 | | 1.854 |
| | 22:29 | 2.608 | |
| | 22:35 | 2.622 | |
| | 22:41 | 2.631 | |
| | 22:47 | 2.630 | |
| | 22:53 | 2.630 | |
| | 22:59 | 2.622 | |
| 5/31/96 | 00:38 | | 1.858 |
| | 00:44 | | 1.853 |
| | 00:50 | | 1.847 |
| | 00:56 | | 1.850 |
| | 01:02 | | 1.853 |
| | 02:32 | 2.594 | |
| | 02:38 | 2.608 | |
| | 02:44 | 2.612 | |
| | 02:50 | 2.625 | |
| | 02:56 | 2.613 | |
| | 03:02 | 2.621 | |
| | 04:33 | | 1.859 |
| | 04:39 | | 1.856 |

TABLE 1-continued

Data Used to Calculate Stream water BDOC Concentration

| | | TOC (mgC/L) | |
|---|---|---|---|
| Date | Time | In | Out |
| | 04:45 | | 1.860 |
| | 04:51 | | 1.861 |
| | 04:57 | | 1.910 |
| | 05:03 | 2.588 | |
| | 06:33 | 2.600 | |
| | 06:39 | 2.606 | |
| | 06:51 | 2.613 | |
| | 06:57 | 2.615 | |
| | 07:03 | 2.623 | |
| | 08:21 | | 1.862 |
| | 08:27 | | 1.853 |
| | 08:33 | | 1.852 |

While not shown, alternately, several TOCin readings with IC present (that is, water from the inflow) can be taken at six minute intervals over the course of an hour and an average value of μg C/l can be obtained for ICin. During the next hour, several TOCout readings with the IC present (that is water from the outflow) can be taken in about six minute intervals and an average value of μg C/l can be obtained for ICout. As pointed out above, the IC concentration can be used as a check on the biological activity of the biofilm.

EXAMPLE 2

Dissolved oxygen can also be measured by the bioreactor apparatus. The oxygen monitoring system described above was utilized by first calibrating the electrodes by bypassing the reactor, closing off valve 148, and using $O_2$ saturated water 151 from the calibration line 150. For optimal results, a calibration check was performed on the electrodes after each reading. The electrode used was a Clark-style polarographic electrode (Ag/AgCl). The flow rate, temperature, and pressure are kept constant, then more accurate results can be obtained. The values of dissolved oxygen concentrations are indicated in mm Hg and the following formula is used to convert the result to mg/l:

$$X = \frac{pO_2(mmHg) \cdot 1.778 \cdot 10^3}{5.996 \cdot 10^5 \cdot T(^\circ C.) + 2.011 \cdot 10^7} \text{ in mg/l}$$

The amplifier takes the reading from the electrode and provides a measurement of the oxygen level in the sample. A valve is provided and is switched to permit inflow and outflow readings to be made.

Other modifications consistent with the scope of the invention described herein may also be made. For example, while not shown, it is understood that filters may be used to remove large particles of debris from the water flow to the columns. The filtration may be done in line before the entry to the column or analyzers or can be done in the line feeding the stream water to the reactor. In addition while two columns are shown, the apparatus may comprise additional columns, as well, or a single column may be used. The valves can be manually or electronically operated and can also be controlled with a timer.

What is claimed is:

1. A method for determining the concentration of biodegradable dissolved organic carbon contaminants in a water system, comprising the steps of:

a) providing a flow path for water to be analyzed, said flow path including an inflow path and an outflow path;

b) establishing a biofilm consisting of microbes from said water system whose biodegradable dissolved organic carbon is to be determined, wherein establishing said biofilm includes flowing said stream water through said apparatus along a zone of said flow path, said zone being provided between said inflow path and said outflow path;

c) providing along said flow path first flow regulation means for regulating the flow of water to the zone containing the biofilm;

d) flowing said water through said first flow regulation means;

e) flowing said water through the zone of the flow path at which said biofilm is contained;

f) flowing water out from the zone of the flow path at which said biofilm is contained through a second flow regulation means, wherein said first and second flow regulation means facilitate an even dispersion of water through the zone of the flow path;

g) measuring with measuring means the concentration of dissolved organic carbon of the flow water DOCin, prior to the flow water entering the zone containing the biofilm;

h) measuring with measuring means the concentration of dissolved organic carbon of the flow water DOCout, after the flow water has passed through the zone containing the biofilm; and i) subtracting the DOCout reading from the DOCin reading to obtain a measurement of biodegradable dissolved organic carbon concentration of the water sample; wherein the step of establishing a biofilm along said zone of flow path includes providing a material in said zone for enabling microbes present in said water system to attach to said material and flowing water from said water system to be analyzed through said first flow regulation means and to said material in said zone.

2. The method of claim 1, wherein the flow of water through the zone containing the biofilm is moved through the zone at a flow rate which enables the biofilm to act upon the components in the water stream.

3. The method of claim 2, wherein the flow rate is from about b 2to 4 ml/min.

4. The method of claim 1, wherein step g) includes obtaining an inflow sample from the inflow path.

5. The method of claim 4, further including the steps of delivering said inflow sample to an analyzer, and measuring the dissolved organic carbon content of the sample.

6. The method of claim 1, wherein step h) includes obtaining an outflow sample from the outflow path.

7. The method of claim 1, further including the step of regulating with timer means the selection of sample inflow and sample outflow to be measured by the measuring means, and alternately measuring DOCin and DOCout concentrations of a water sample.

8. The method of claim 1, further including the step of flowing sample through an inorganic carbon removal module prior to measuring DOCin and DOCout.

9. The method of claim 1, further including the step of flowing sample through an oxygen analyzer module to determine the amount of oxygen in the water sample.

* * * * *

UNITED STATES PATENT AND TRADEMARK OFFICE
CERTIFICATE OF CORRECTION

PATENT NO. : 6,033,568
DATED : March 7, 2000
INVENTOR(S) : Louis A. Kaplan

It is certified that error appears in the above-identified patent and that said Letters Patent are hereby corrected as shown below:

Col. 1, line 9 "5,873,497" should be deleted and replaced with - -5,873,997- -.
Col. 6, line 3 "stream well" should be deleted and replaced with - -stream, well- -.
Col. 9, line 63 "18" should be deleted and replaced with - -118- -.
Col. 12, line 46 "about b 2to 4 ml/min." should be deleted and replaced with - -about 2 to 4 ml/min.- -.

Signed and Sealed this

Third Day of April, 2001

*Attest:*

NICHOLAS P. GODICI

*Attesting Officer*     Acting Director of the United States Patent and Trademark Office